(12) United States Patent
Koshizen et al.

(10) Patent No.: US 8,044,808 B2
(45) Date of Patent: Oct. 25, 2011

(54) SYSTEM AND METHOD FOR ESTIMATING INTEREST LEVEL

(75) Inventors: Takamasa Koshizen, Saitama (JP); Kazuyuki Aihara, Tokyo (JP); Motohri Kon, Tokyo (JP)

(73) Assignee: Honda Motor Co., Ltd., Tokyo (JP)

( * ) Notice: Subject to any disclaimer, the term of this patent is extended or adjusted under 35 U.S.C. 154(b) by 426 days.

(21) Appl. No.: 12/385,453

(22) Filed: Apr. 8, 2009

(65) Prior Publication Data
US 2009/0262973 A1   Oct. 22, 2009

(30) Foreign Application Priority Data
Apr. 9, 2008   (JP) .................. 2008-101940

(51) Int. Cl.
*G08B 23/00* (2006.01)

(52) U.S. Cl. ........ 340/576; 340/575; 340/436; 340/438; 340/573.1; 382/104; 382/107; 382/154

(58) Field of Classification Search .......... 340/576, 340/575, 425.5, 436, 438, 573.1; 382/103, 382/104, 107, 154; 600/300, 301
See application file for complete search history.

(56) References Cited

U.S. PATENT DOCUMENTS

| | | | |
|---|---|---|---|
| 5,682,144 A * | 10/1997 | Mannik | 340/575 |
| 6,265,978 B1 * | 7/2001 | Atlas | 340/575 |
| 7,792,328 B2 * | 9/2010 | Albertson et al. | 382/104 |
| 2004/0208496 A1 * | 10/2004 | Pilu | 396/263 |

FOREIGN PATENT DOCUMENTS

| | | |
|---|---|---|
| JP | 2005-006897 | 1/2005 |
| JP | 2005-237561 | 9/2005 |
| JP | 2006-020131 | 1/2006 |

* cited by examiner

*Primary Examiner* — Hung T. Nguyen
(74) *Attorney, Agent, or Firm* — Squire, Sanders & Dempsey (US) LLP (57) ABSTRACT

The interest level estimation system of the present invention includes a gaze measurement unit that measures a person's gaze velocity and a skin potential level measurement unit that measures a person's skin potential level. The interest level estimation system also includes an interest level estimation unit. In the interest level estimation unit, a skin potential level time variation and a gaze velocity standard deviation are obtained at predetermined intervals, an inflection point of the skin potential level time variation is obtained at the predetermined intervals, the skin potential level time variation and the gaze velocity standard deviation that are obtained before a time corresponding to the inflection point are related to an interest state at the predetermined intervals, and the skin potential level time variation and the gaze velocity standard deviation that are obtained after the time corresponding to the inflection point are related to a disinterest state at the predetermined intervals, thereby obtaining a relationship between the skin potential level time variation and gaze velocity standard deviation and the interest level.

6 Claims, 10 Drawing Sheets

SYSTEM AND METHOD FOR ESTIMATING INTEREST LEVEL

BACKGROUND OF THE INVENTION

1. Field of the Invention

The present invention relates to an interest level estimation system and an interest level estimation method for estimating a person's interest level to a subject.

2. Description of the Related Art

A system which measures a person's interest level to contents from a person's eye movement has been developed as a system and a method for estimating the person's interest level to the subject (for example, see Japanese Patent Application Laid-Open No. 2006-20131). However, it is not always suitable that the person's interest level to the subject is estimated by only a measurement value relating to the person's eye movement. Sometimes the person's interest level is changed with time even in the similar subject. A phenomenon in which the interest level (reactivity) to the similar subject is lowered by acclimatization is referred to as habituation. On the contrary, a phenomenon in which the interest level (reactivity) to the similar subject is increased is referred to as dishabituation. A change in the person's interest level with time is not sufficiently considered in the conventional system and method for the interest level.

Thus, the interest level estimation system and interest level estimation method in which the person's interest level is estimated in consideration of a change of the interest level with time (time-inconsistency of interest level) using suitable measurement values indicating the person's interest level is not developed.

Accordingly, there is a need for the interest level estimation system and interest level estimation method in which the person's interest level is estimated in adequate consideration of a change in the interest level with time using suitable measurement values indicating the interest level.

SUMMARY OF THE INVENTION

In accordance with a first aspect of the invention, an interest level estimation system which estimates a person's interest level includes a gaze measurement unit that measures a person's gaze velocity; a skin potential level measurement unit that measures a person's skin potential level; and an interest level estimation unit that obtains a skin potential level time variation and a gaze velocity standard deviation at predetermined intervals, obtains an inflection point of the skin potential level time variation at the predetermined intervals, relates the skin potential level time variation and the gaze velocity standard deviation that are obtained before a time corresponding to the inflection point to an interest state at the predetermined intervals, relates the skin potential level time variation and the gaze velocity standard deviation that are obtained after the time corresponding to the inflection point to a disinterest state at the predetermined intervals, and thus obtains a relationship between the skin potential level time variation and gaze velocity standard deviation and the interest level.

In accordance with a second aspect of the invention, an interest level estimation method for estimating a person's interest level includes obtaining a person's skin potential level time variation and a gaze velocity standard deviation at predetermined intervals; obtaining an inflection point of the skin potential level time variation at the predetermined intervals; relating the skin potential level time variation and the gaze velocity standard deviation that are obtained before a time corresponding to the inflection point to an interest state at the predetermined intervals; relating the skin potential level time variation and the gaze velocity standard deviation that are obtained after the time corresponding to the inflection point to a disinterest state at the predetermined intervals; and thus obtaining a relationship between the skin potential level time variation and gaze velocity standard deviation and the interest level.

Accordingly, in the invention, the person's interest level can be estimated in adequate consideration of a change in the interest level with time using the two variables of the skin potential level time variation and the gaze velocity standard deviation.

DETAILED DESCRIPTION OF THE INVENTION

Figure 1:
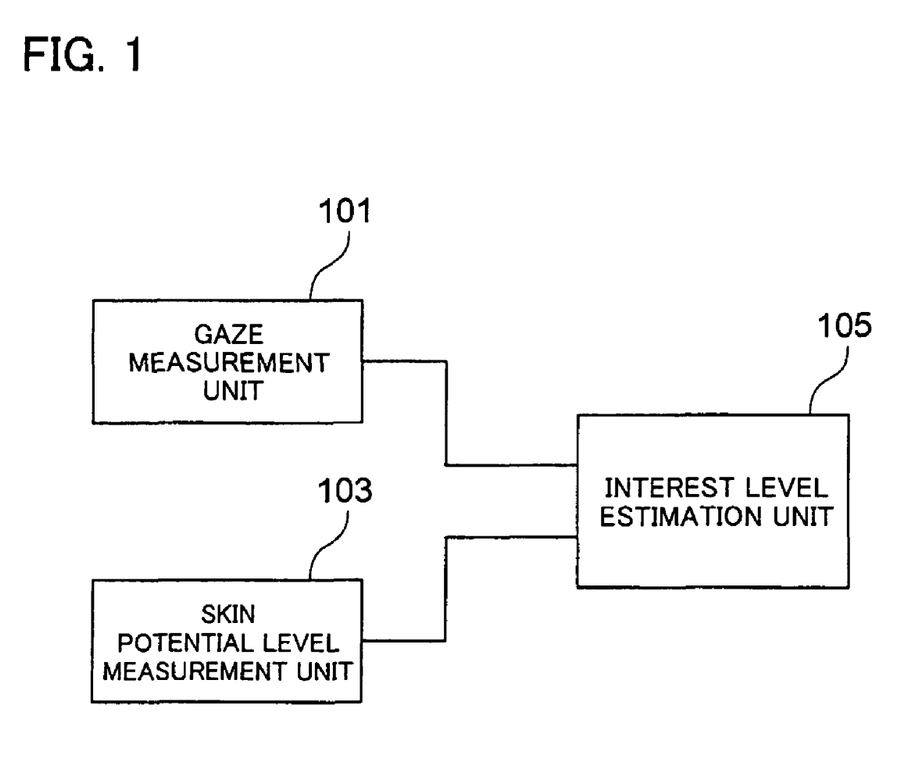
FIG. 1 illustrates a configuration of an interest level estimation system according to an embodiment of the invention.

FIG. 1 illustrates a configuration of an interest level estimation system according to an embodiment of the invention. The interest level estimation system includes a gaze measurement unit 101, a skin potential level measurement unit 103, and an interest level estimation unit 105.

The gaze measurement unit 101 of the embodiment includes a stereo camera that takes an image of a subject face and a processor that processes the image to measure eye gaze of the subject. The processor includes a face detection module and a face measurement module. The face detection module extracts a face region from a pair of stereo images using a face standard edge template. The face measurement module detects information on the face including the eye gaze. In order to measure the eye gaze, first a center position of an eyeball is computed. Then a radius of the eyeball and a position of an iris are computed. Finally the eye gaze is estimated by an offset of the position of the iris from the center position of the eyeball. The gaze measurement unit 101 computes a gaze vector to within five degrees of accuracy for about 10 milliseconds. Eye-gaze data is obtained in two-dimensional coordinate such as (x,y).

The skin potential level measurement unit 103 of the embodiment measures a skin potential level used to quantify an alertness level of the subject. A sampling rate ranges from 10 to 100 Hz.

Figure 2:
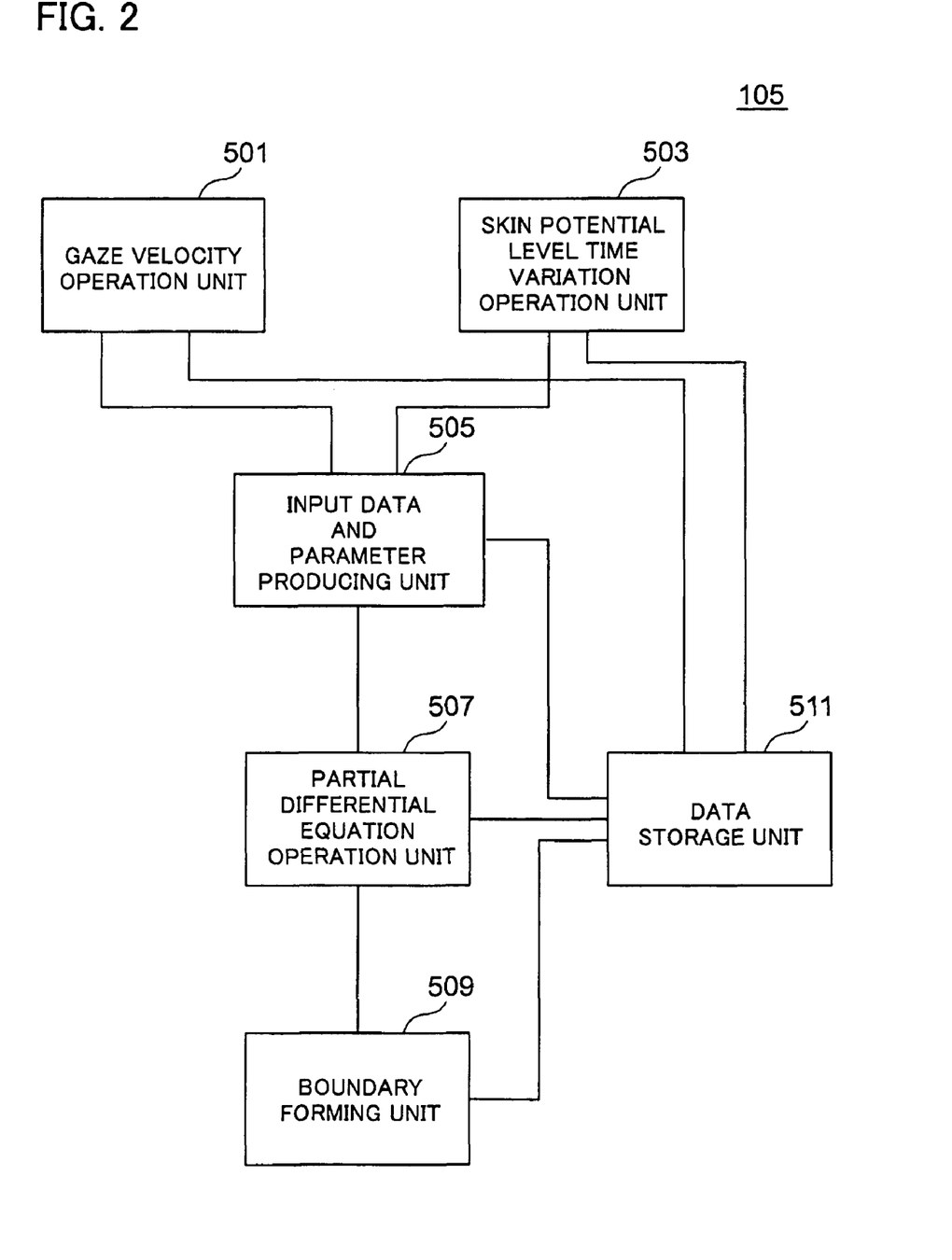
FIG. 2 illustrates a configuration of an interest level estimation unit in the interest level estimation system of the embodiment.

FIG. 2 illustrates a configuration of the interest level estimation unit 105 in the interest level estimation system of the embodiment. The interest level estimation unit 105 includes a gaze velocity operation unit 501, a skin potential level time variation operation unit 503, an input data and parameter producing unit 505, a partial differential equation operation unit 507, a boundary forming unit 509, and a data storage unit 511.

The gaze velocity operation unit 501 obtains a gaze velocity at predetermined intervals by an operation based on the eye-gaze data that is measured by the gaze measurement unit 101 and stored in the data storage unit 511.

The skin potential level time variation operation unit 503 performs obtains a skin potential level time variation at predetermined intervals by an operation based on the skin potential level data that is measured by the skin potential level measurement unit 103 and stored in the data storage unit 511. In obtaining the skin potential level time variation by the operation, a noise of the measured skin potential level data is reduced with a lowpass filter such as a Butterworth filter.

The input data and parameter producing unit 505 produces input data and a parameter of a partial differential equation based on the data stored in the data storage unit 511. The input data and parameter producing unit 505 transmits the produced input data and parameter to the partial differential equation operation unit 507.

The partial differential equation operation unit 507 performs an operation of the partial differential equation based on the input data and parameter produced by the input data and parameter producing unit 505 and past data stored in the data storage unit 511. At this point, the partial differential equation describes an unknown function u of variables (x,y) in a later-mentioned normalized two-dimensional space and time. In the embodiment, the following Allen-Cahn equation is used as the partial differential equation:

$$\frac{\partial u}{\partial t} = \Delta u - \frac{1}{\varepsilon^2} \frac{d\omega(u)}{du} \qquad (1)$$

$$\omega(u) = \frac{1}{2}(1 - u^2)^2 \qquad (2)$$

where $\varepsilon$ is a parameter and $\omega(u)$ is a double-well potential equation in which two minimum values are related to two different phases. When the parameter $\varepsilon$ is brought close to zero, the unknown function u is brought close to one of the two minimum values, that is, 1 and −1 in the two regions separated by the boundary. The boundary is expressed by a line of u=0. In the embodiment, the interest state and the disinterest state is separated by the boundary in the normalized two-dimensional space.

The partial differential equation operation unit 507 performs an operation of a value of the unknown function u in the normalized two-dimensional space based on the input data that is received as time advances, and the partial differential equation operation unit 507 stores the value of the unknown function u in the data storage unit 511 while transmitting the value of the unknown function u to the boundary forming unit 509.

The boundary forming unit 509 defines a boundary between the interest state and the disinterest state in the normalized two-dimensional space based on the value of the unknown function u in the normalized two-dimensional space that is received from the partial differential equation operation unit 507.

An interest level estimation method according to an embodiment of the invention will be described below along with detailed functions of the input data and parameter producing unit 505, partial differential equation operation unit 507, and boundary forming unit 509.

Figure 3:
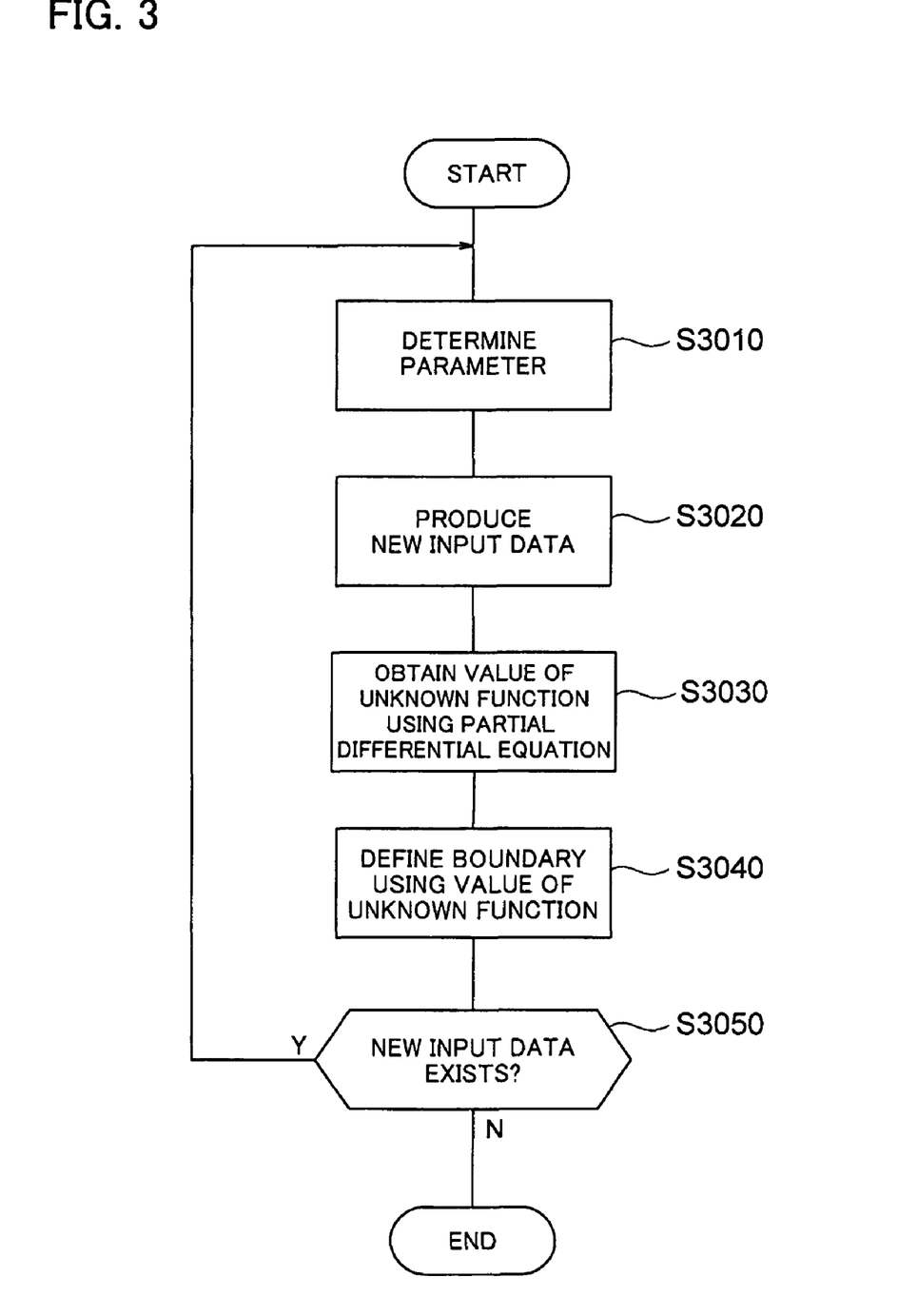
FIG. 3 is a flowchart illustrating an interest level estimation method according to an embodiment of the invention.

FIG. 3 is a flowchart illustrating an interest level estimation method according to an embodiment of the invention.

Referring to FIG. 3, in Step S3010, the input data and parameter producing unit 505 determines a value of the parameter $\varepsilon$ in the equation (1) according to the following equation:

$$\varepsilon = \alpha + \exp(-\lambda\tau) \qquad (3)$$

where $\alpha$ and $\lambda$ are constants and $\tau$ is the number of bins (the number of pieces of input data on the normalized two-dimensional space). Initially $\tau$ is set at 1. Because $\tau$ is increased as the new input data is added, the value of the parameter $\varepsilon$ is decreased.

In Step S3020 of FIG. 3, the input data and parameter producing unit 505 produces the input data of the partial differential equation based on the data stored in the data storage unit 511.

Figure 4:
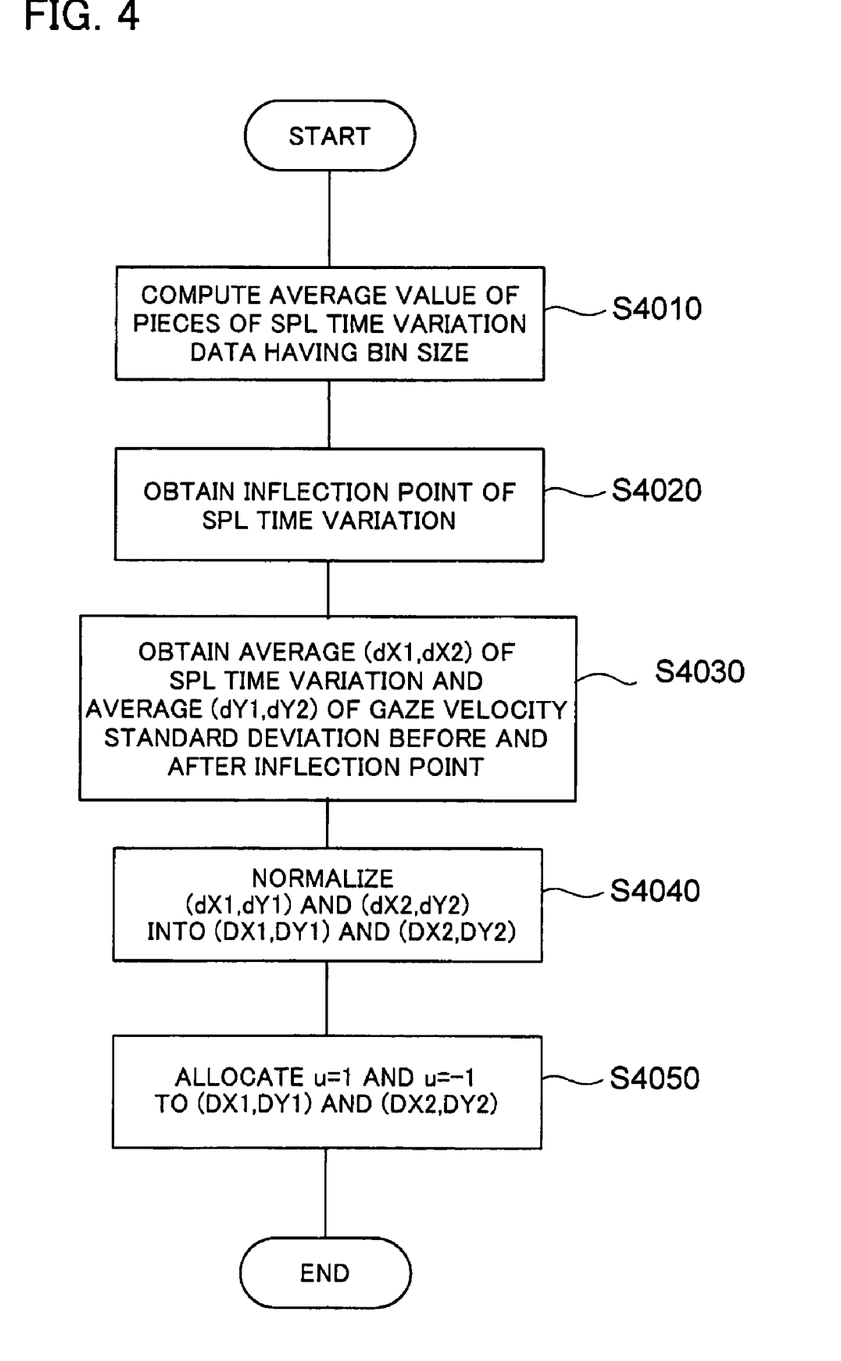
FIG. 4 is a flowchart explaining detail processing in Step S3020 of FIG. 3.

FIG. 4 is a flowchart for explaining the detailed method in Step S3020 of FIG. 3.

Figure 5:
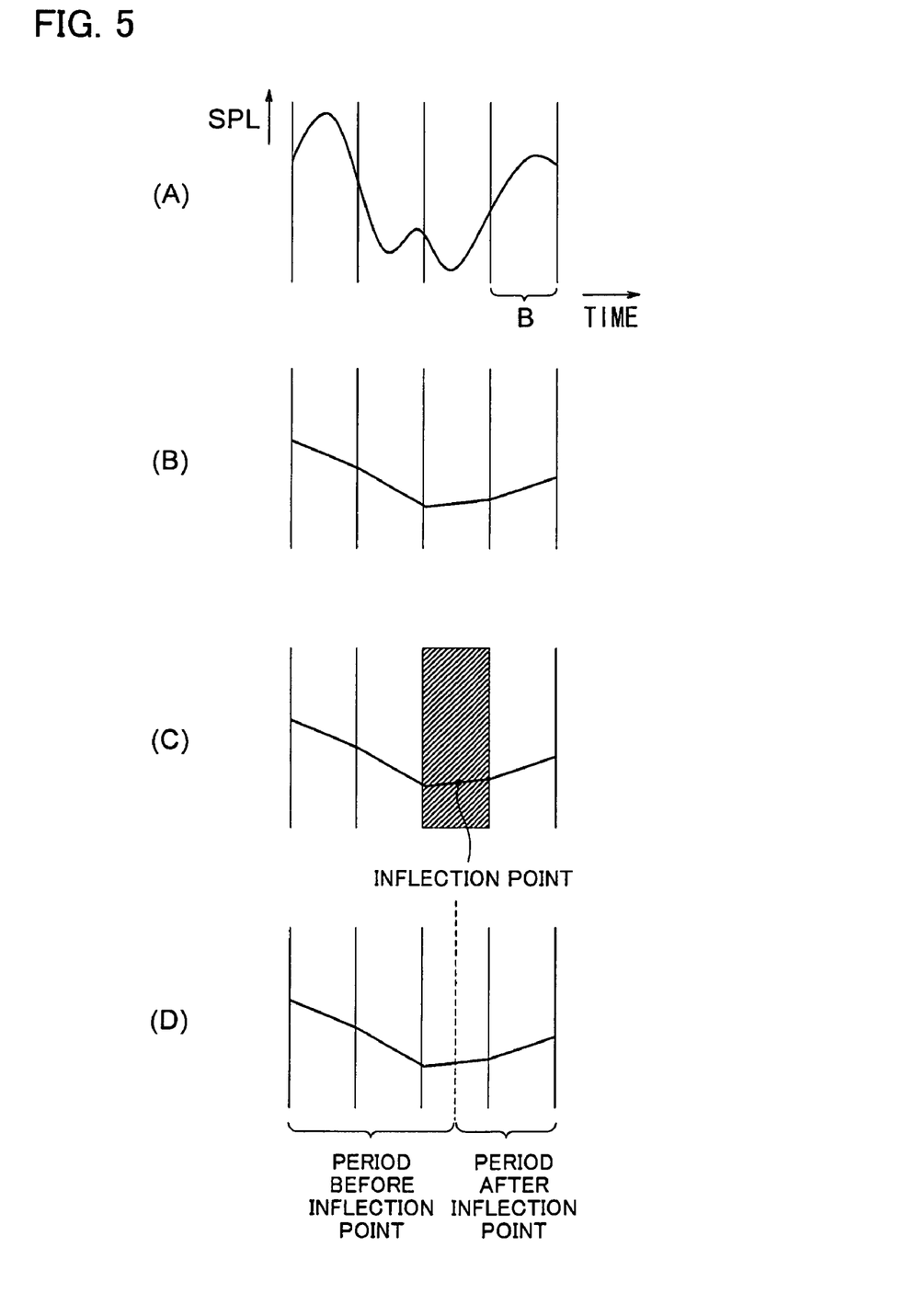
FIG. 5 explains the processing of FIG. 4.

FIG. 5 is a view for explaining the method of FIG. 4. In FIG. 5, a horizontal axis indicates passage of time, and a vertical axis indicates magnitude of a Skin Potential Level (SPL).

Referring to FIG. 4, in Step S4010, the skin potential level time variation operation unit 503 reads the pieces of data of the skin potential level (SPL) corresponding to the number indicating bin size B as new input data from the data storage unit 511, and the skin potential level time variation operation unit 503 computes an average value of the skin potential level time variations (see FIGS. 5A and 5B). At this point, the number indicating the bin size is 200 by way of example. The data sampling interval is set at 0.1 second and a time interval in which an average value is computed is set at 20 seconds by way of example. The average value of the skin potential level time variations is stored in the data storage unit 511.

In Step S4020 of FIG. 4, the input data and parameter producing unit 505 obtains a median from average values of the skin potential level time variation for respective bins stored in the data storage unit 511. When the number of the bins is of an even number, the smaller value in the two average values is set at the median. A point corresponding to an intermediate position of the horizontal axis (time axis) of the bin including the median is set at an inflection point (see FIG. 5C).

In Step S4030 of FIG. 4, the skin potential level time variation operation unit 503 obtains average values (dx1,dx2) of the skin potential level time variations in a period prior to the inflection point and a period after the inflection point based on the inflection point data and the skin potential level data stored in the data storage unit 511. The gaze velocity operation unit 501 obtains average values (dy1,dy2) of the gaze velocity standard deviation in the period prior to the inflection point and the period after the inflection point based on the inflection point data and the eye-gaze data stored in the data storage unit 511 (FIG. 5D). The pieces of data (dx1,dx2) and (dy1,dy2) are transmitted to the input data and parameter producing unit 505.

In Step S4040 of FIG. 4, the input data and parameter producing unit 505 normalizes the pieces of data (dx1,dy1)

into pieces of data (DX1,DY1), and the input data and parameter producing unit 505 normalizes the pieces of data (dx2, dy2) into pieces of data (DX2,DY2). In actually performing the normalization, a sufficiently large range where all the variables are included is defined, and the range is divided into 200 segments, for example. Then, variables are respectively allocated to the segments. Thus, the two-dimensional space formed by the normalized skin potential level time variation and the gaze velocity standard deviation is referred to as normalized two-dimensional space.

In Step S4050 of FIG. 4, u=1 is allocated to (DX1,DY1), and u=−1 is allocated to (DX2,DY2). It is assumed that a pair of pieces of data fed in the normalized two-dimensional space is one piece of input data. u=1 corresponds to the interest state while u=−1 corresponds to the disinterest state. As described above, one piece of input data corresponds to the bin size measurement data.

Referring to FIG. 3, in Step S3030, the partial differential equation operation unit 507 obtains the value of the unknown function u in the normalized two-dimensional space by solving the partial differential equation of the equations (1) and (2) for a time corresponding to the number of pieces of input data (that is, the number of bins). At this point, the normalized two-dimensional space is discretized, and a Laplacian is computed by five-point approximation.

In Step S3040 of FIG. 3, the boundary forming unit 509 defines a line along which u=0 is established in the normalized two-dimensional space as the boundary between the interest state and the disinterest state.

In Step S3050 of FIG. 3, the input data and parameter producing unit 505 determines whether or not new input data exists. The flow returns to Step S3010 when new input data exists, and the processing is ended when new input data does not exist.

Figure 6:
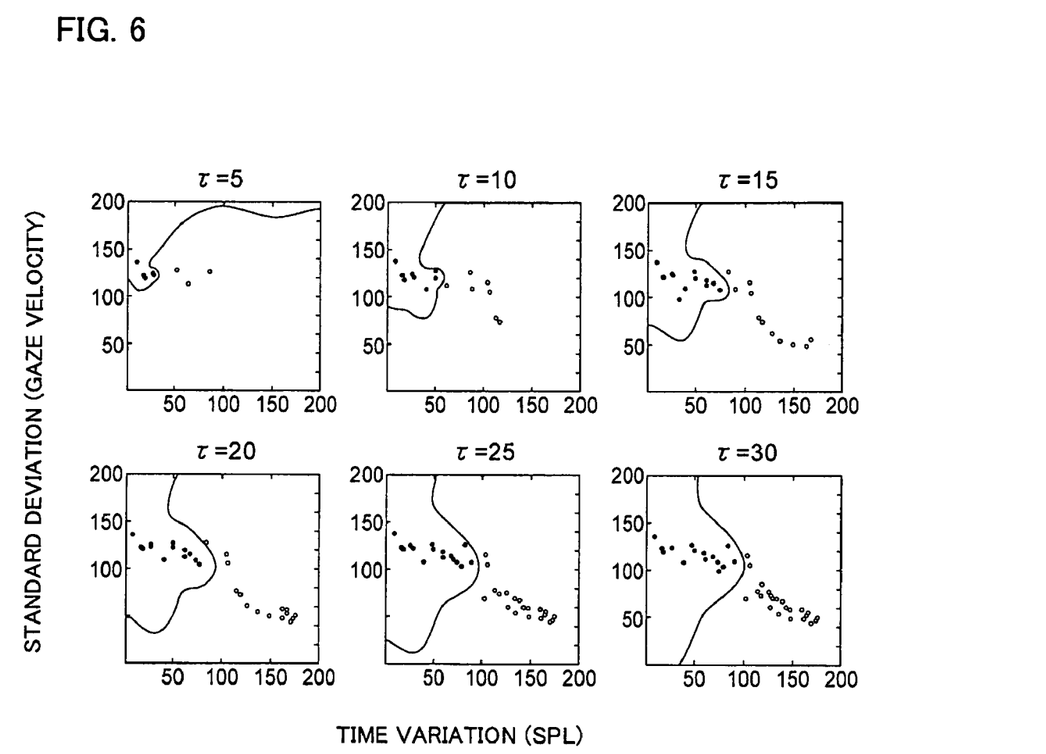
FIG. 6 illustrates a change with time, estimated by the method of the embodiment, in a boundary between an interest state and a disinterest state in a normalized two-dimensional space.

FIG. 6 illustrates a change with time, estimated by the method of the embodiment, in a boundary between the interest state and the disinterest state in the normalized two-dimensional space. In FIG. 6, the boundary is indicated by a solid line, a black point indicates a point of u>0, and a white point indicates a point of u<0. τ indicates the number of pieces of input data. As the number of pieces of input data is increased, the region on the left side of the boundary (the interest region) is expanded toward the right.

Figure 7:
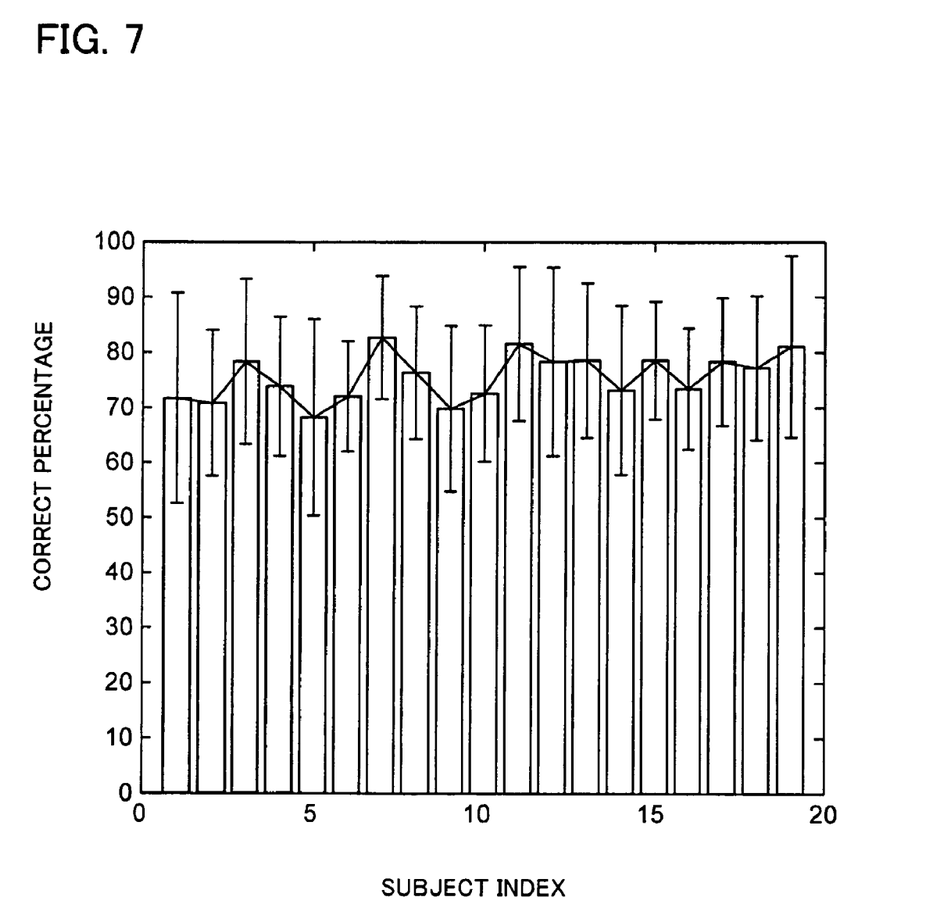
FIG. 7 illustrates a correct percentage of an interest level in each subject, which is estimated by the method of the embodiment.

FIG. 7 illustrates a correct percentage of an interest level in each subject, which is estimated by the method of the embodiment. The horizontal axis indicates a subject index. The subjects include 19 persons (17 men and two women), the age of the subjects ranges from late twenties to mid-sixties. The experiment is performed such that the subject experiences on-road driving for five minutes with an automobile driving simulator. The vertical axis indicates a correct percentage of an interest level. Correctness is determined based on whether or not a label (that is, u=1 or u=−1) of the point that is newly plotted in the normalized two-dimensional space is matched with an original label of the point. That is, the correct percentage is computed such that a correct answer is obtained when the label of the newly added point is matched with the original label while incorrect answer is obtained when the label of the newly added point is not matched with the original label. The value of the parameter $\epsilon$ of the equation (1) is changed to obtain a correct percentage computed for each value of the parameter $\epsilon$. An average of correct percentage values corresponding to the changed values of the parameter $\epsilon$ is set at the correct percentage of FIG. 7, while a standard deviation is set at an error bar in FIG. 7.

Figure 8:
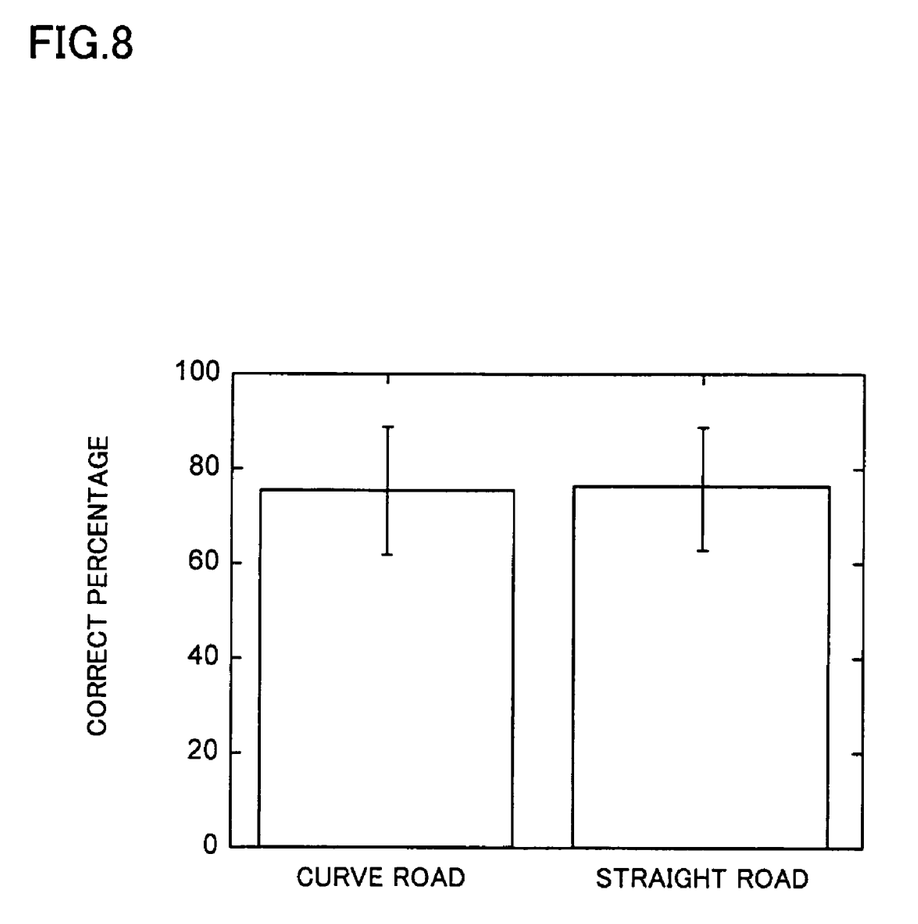
FIG. 8 illustrates a correct percentage of an interest level in each kind of a road, which is estimated by the method of the embodiment.
Figure 10:
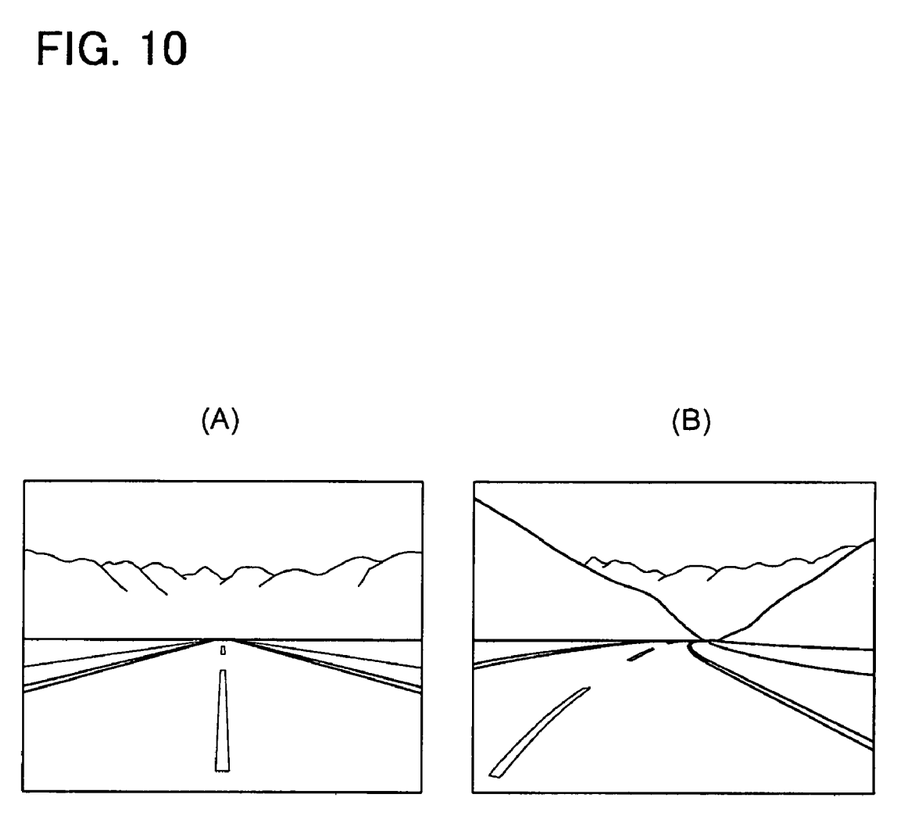
FIG. 10 illustrates an example of an image of an automobile driving simulator.

FIG. 8 illustrates a correct percentage of an interest level in each kind of the road, which is estimated by the method of the embodiment. The horizontal axis indicates a kind of the load. FIG. 10 illustrates an example of the image of the automobile driving simulator. The left of FIG. 10 illustrates an image of a straight road, and the right indicates an image of a curve road. The left of FIG. 8 indicates the correct percentage on the curve road (the right of FIG. 10) of the automobile driving simulation performed by all the subjects. The right of FIG. 8 indicates the correct percentage on the straight road (the left of FIG. 10) of the automobile driving simulation performed by all the subjects. The correct percentage and the error bar are obtained in the way similar to that of FIG. 7.

Figure 9:
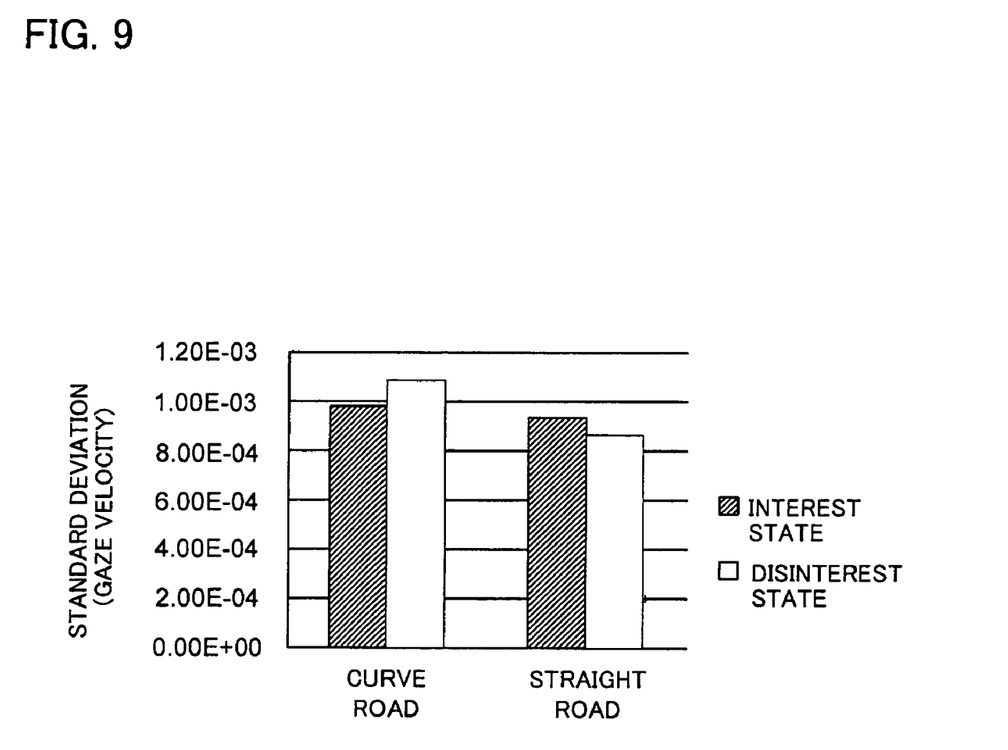
FIG. 9 illustrates a relationship between a standard deviation of a gaze velocity and the interest state and the disinterest state which are estimated by the method of the embodiment.

FIG. 9 illustrates a relationship between the interest state and disinterest state which are estimated by the method of the embodiment and the standard deviation of the gaze velocity. The horizontal axis indicates the kind of the load. The left of FIG. 9 indicates a relationship between the interest state and disinterest state and the standard deviation of the gaze velocity on the curve road (the right of FIG. 10) of the automobile driving simulation performed by all the subjects. The right of FIG. 9 indicates a relationship between the interest state and disinterest state and the standard deviation of the gaze velocity on the straight road (the left of FIG. 10) of the automobile driving simulation performed by all the subjects. The vertical axis indicates the standard deviation of the gaze velocity. In FIG. 9, a bar marked with diagonal lines indicates the interest state. The disinterest state is larger than the interest state in the standard deviation of the gaze velocity on the curve road. This is attributed to the fact that the subject who has entered the disinterest state due to the dishabituation more broadly views the curve road. On the other hand, the disinterest state is smaller than the interest state in the standard deviation of the gaze velocity on the straight road. This is attributed to the fact that the subject who has entered the disinterest state due to the dishabituation blankly views the straight road.

Thus, in the embodiment, the change in person's interest level with time can appropriately be estimated.

The embodiment of the invention has the following features.

In one embodiment of the invention, the Allen-Cahn equation of the unknown function u in the normalized two-dimensional plane in which the normalized skin potential level time variation and the standard deviation of the normalized gaze velocity are set as variables is used, when the skin potential level time variation and the standard deviation of the gaze velocity that are obtained before the time corresponding to the inflection point are related to the interest state at predetermined time intervals while the skin potential level time variation and the standard deviation of the gaze velocity that are obtained after the time corresponding to the inflection point are related to the disinterest state at the predetermined time intervals.

In the embodiment, the time-inconsistent boundary between the interest state and the disinterest state can appropriately be estimated using the Allen-Cahn equation of the unknown function u in the normalized two-dimensional plane in which the normalized skin potential level time variation and the standard deviation of the normalized gaze velocity are set as variables.

In another embodiment of the invention, the pair of points on the normalized two-dimensional plane is obtained at the predetermined intervals. The pair of points includes the point on the normalized two-dimensional plane related to the average value of the skin potential level time variation and the average value of the gaze velocity standard deviation that are obtained before the time corresponding to the inflection point and the point on the normalized two-dimensional plane related to the average value of the skin potential level time variation and the average value of the gaze velocity standard deviation that are obtained after the time corresponding to the inflection point. Then the Allen-Cahn equation is solved at the predetermined intervals by imparting positive and negative predetermined values to the unknown function u of the pair of points. Therefore, the interest state and the disinterest state are distinguished from each other by the line of u=0 on the normalized two-dimensional plane.

In the embodiment, the Allen-Cahn equation is solved at the predetermined intervals by imparting positive and negative predetermined values to the unknown function u of the pair of points obtained on the normalized two-dimensional plane, and the interest state and the disinterest state are distinguished from each other by the line of u=0 on the normalized two-dimensional plane, so that the time-inconsistent boundary between the interest state and the disinterest state can appropriately be estimated. The estimation of the time-inconsistent boundary cannot efficiently be performed by the conventional method in which the Support Vector Machine (SVM) is used.

We claim:

1. An interest level estimation system which estimates a person's interest level, comprising:
   a gaze measurement unit that measures a person's gaze velocity;
   a skin potential level measurement unit that measures a person's skin potential level; and
   an interest level estimation unit that obtains a skin potential level time variation and a gaze velocity standard deviation at predetermined intervals, obtains an inflection point of the skin potential level time variation at the predetermined intervals, relates the skin potential level time variation and the gaze velocity standard deviation that are obtained before a time corresponding to the inflection point to an interest state at the predetermined intervals, relates the skin potential level time variation and the gaze velocity standard deviation that are obtained after the time corresponding to the inflection point to a disinterest state at the predetermined intervals, and thus obtains a relationship between the skin potential level time variation and gaze velocity standard deviation and the interest level.

2. The interest level estimation system according to claim 1, wherein an Allen-Cahn equation of an unknown function u in a normalized two-dimensional plane in which the normalized skin potential level time variation and the normalized gaze velocity standard deviation are set as variables is used when the interest level estimation unit relates the skin potential level time variation and the gaze velocity standard deviation that are obtained before the time corresponding to the inflection point to the interest state at the predetermined intervals and relates the skin potential level time variation and the gaze velocity standard deviation that are obtained after the time corresponding to the inflection point to the disinterest state at the predetermined intervals.

3. The interest level estimation system according to claim 2, wherein the interest level estimation unit obtains a pair of points on the normalized two-dimensional plane at the predetermined intervals, the pair of points including a point on the normalized two-dimensional plane related to an average value of the skin potential level time variation and an average value of the gaze velocity standard deviation that are obtained before the time corresponding to the inflection point and a point on the normalized two-dimensional plane related to an average value of the skin potential level time variation and an average value of the gaze velocity standard deviation that are obtained after the time corresponding to the inflection point,
   the interest level estimation unit solves the Allen-Cahn equation at the predetermined intervals by imparting positive and negative predetermined values to the unknown function u of the pair of points, and
   the interest level estimation unit distinguishes the interest state and the disinterest state from each other by a line of u=0 on the normalized two-dimensional plane.

4. An interest level estimation method for estimating a person's interest level, comprising:
   obtaining a person's skin potential level time variation and a gaze velocity standard deviation at predetermined intervals;
   obtaining an inflection point of the skin potential level time variation at the predetermined intervals;
   relating the skin potential level time variation and the gaze velocity standard deviation that are obtained before a time corresponding to the inflection point to an interest state at the predetermined intervals;
   relating the skin potential level time variation and the gaze velocity standard deviation that are obtained after the time corresponding to the inflection point to a disinterest state at the predetermined intervals; and
   thus obtaining a relationship between the skin potential level time variation and gaze velocity standard deviation and the interest level.

5. The interest level estimation method according to claim 4, wherein an Allen-Cahn equation of an unknown function u in a normalized two-dimensional plane in which the normalized skin potential level time variation and the normalized gaze velocity standard deviation are set as variables is used when the skin potential level time variation and the gaze velocity standard deviation that are obtained before the time corresponding to the inflection point are related to the interest state at the predetermined intervals and the skin potential level time variation while the gaze velocity standard deviation that are obtained after the time corresponding to the inflection point are related to the disinterest state at the predetermined intervals.

6. The interest level estimation method according to claim 5, wherein the pair of points on the normalized two-dimensional plane is obtained at the predetermined intervals, the pair of points including a point on the normalized two-dimensional plane related to an average value of the skin potential level time variation and an average value of the gaze velocity standard deviation that are obtained before a time corresponding to the inflection point and the point on the normalized two-dimensional plane related to an average value of the skin potential level time variation and an average value of the gaze velocity standard deviation that are obtained after a time corresponding to the inflection point,
   the Allen-Cahn equation is solved at the predetermined intervals by imparting positive and negative predetermined values to the unknown function u of the pair of points, and
   the interest state and the disinterest state are distinguished from each other by the line of u=0 on the normalized two-dimensional plane.

* * * * *